(12) United States Patent
Dawood

(10) Patent No.: US 6,341,694 B1
(45) Date of Patent: Jan. 29, 2002

(54) PACKAGING AND COMPONENT DELIVERY SYSTEM FOR USE IN STERILE MEDICAL OR DENTAL PROCEDURES

(75) Inventor: J. S. Andrew Dawood, London (GB)

(73) Assignee: Nobel Biocare AB, Gothenberg (SE)

( * ) Notice: Subject to any disclaimer, the term of this patent is extended or adjusted under 35 U.S.C. 154(b) by 0 days.

(21) Appl. No.: 09/381,354

(22) PCT Filed: Mar. 27, 1998

(86) PCT No.: PCT/SE98/00568

§ 371 Date: Dec. 2, 1999

§ 102(e) Date: Dec. 2, 1999

(87) PCT Pub. No.: WO98/43892

PCT Pub. Date: Oct. 8, 1998

(30) Foreign Application Priority Data

Apr. 3, 1997 (GB) ............................................... 9706796

(51) Int. Cl.⁷ .............................................. B65D 75/64
(52) U.S. Cl. ........................ 206/572; 81/3.56; 206/438; 383/211
(58) Field of Search ................................ 81/3.07, 3.43, 81/3.47–3.49, 3.55, 3.56, 302; 206/363, 438, 370, 570, 571, 572; 383/202, 207, 209, 211; 220/277; 606/1; 422/300; 128/898

(56) References Cited

U.S. PATENT DOCUMENTS

| | | | | |
|---|---|---|---|---|
| 1,319,007 A | * | 10/1919 | Kind | 81/302 |
| 1,461,151 A | * | 7/1923 | Keeler | 220/277 |
| 1,806,339 A | * | 5/1931 | Ferris et al. | 81/302 |
| 3,681,840 A | * | 8/1972 | Pool | 81/302 |
| 3,730,338 A | * | 5/1973 | Chesky | 206/570 |
| 3,981,398 A | * | 9/1976 | Boshoff | 206/570 |
| 4,736,850 A | * | 4/1988 | Bowman et al. | 206/570 |
| 5,040,678 A | * | 8/1991 | Lenmark, Sr. et al. | 206/570 |
| 5,234,106 A | | 8/1993 | Transue et al. | |
| 5,257,692 A | * | 11/1993 | Heacox | 206/210 |
| 5,424,048 A | * | 6/1995 | Riley | 206/438 |
| 5,715,943 A | | 2/1998 | Thompson, Jr. | |
| 5,732,821 A | * | 3/1998 | Stone et al. | 206/370 |
| 5,833,055 A | * | 11/1998 | Cerwin et al. | 206/63.3 |

FOREIGN PATENT DOCUMENTS

EP      0 677 299      4/1995

* cited by examiner

Primary Examiner—Jim Foster
(74) Attorney, Agent, or Firm—Connolly Bove Lodge & Hutz

(57) ABSTRACT

A packaging system is disclosed having a number of packages, a storage tray for containing the number of packages, and an instrument having functional extensions designed to engage, grasp, or mate with an opening formed on the package. Each package is formed of sterilizable packaging material, encloses a sterile item, and has an opening formed on the packaging material for receiving the instrument. An operator carrying out a surgical procedure, using a conventional aseptic surgical technique, uses the instrument to pick up, manipulate, and open the package to deliver the sterile item for use during the procedure.

6 Claims, 3 Drawing Sheets

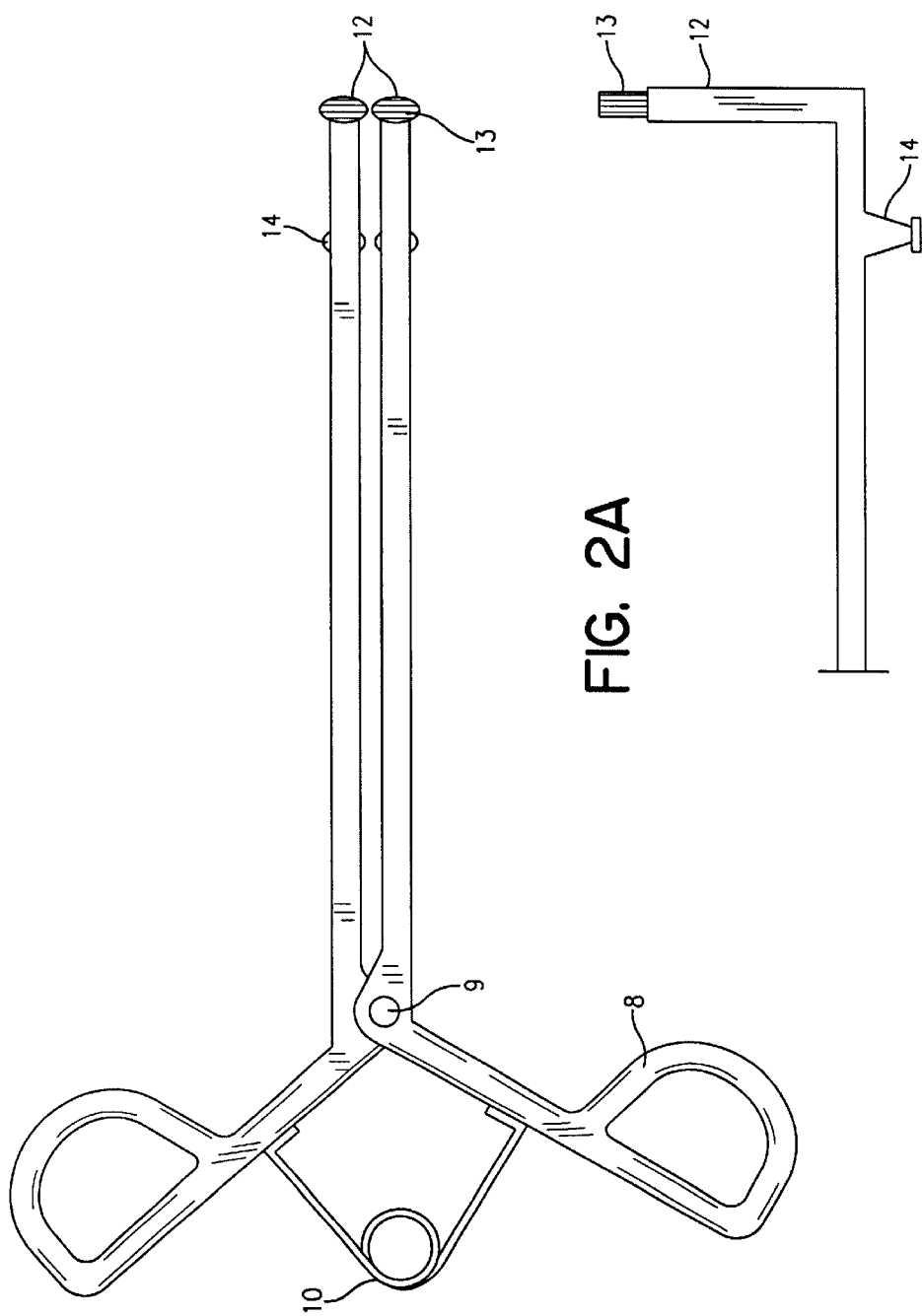

PACKAGING AND COMPONENT DELIVERY SYSTEM FOR USE IN STERILE MEDICAL OR DENTAL PROCEDURES

FIELD OF THE INVENTION

A packaging and component delivery system for use in sterile medical or dental procedures.

BACKGROUND OF THE INVENTION

For many surgical procedures conducted under conventional high standards of cleanliness and sterility (i.e. good aseptic technique), components or materials such as bone screws, implants, dental implants and components, suture materials and wound dressings, must be selected during the course of the procedure.

The surgeon may wear sterile gloves and sterile gown, and it would not be appropriate to handle the non-sterile exterior of a package. In current practice, this problem is usually overcome by asking an assistant who is not otherwise involved in the actual procedure to open the package and tip out the sterile contents onto a sterile surface, or otherwise permit the sterile item to be withdrawn from the packaging.

SUMMARY OF THE INVENTION

The present invention relates to an adaptation of existing packaging systems which will permit a non-sterile package to be selected and opened, and the sterile contents removed and delivered onto a sterile surface. This process may be carried out by the operator working under sterile operating conditions, without compromising the cleanliness or sterility of the procedure. This eliminates the need for an assistant, and facilitates the selection of exactly the items that the operator requires, with minimal interruption of the proceedings.

BRIEF DESCRIPTION OF THE DRAWINGS

FIG. 1A illustrates another embodiment of a rectangular package formed of a sterilized packaging material and containing a sterile item;

FIG. 1B illustrates a further embodiment of a rectangular package formed of a sterilized packaging material and containing a sterile item;

FIGS. 2A and 2B illustrate a preferred embodiment of the instrument used to manipulate and open the package of FIG. 1.

A specific embodiment of the invention will now be described with reference to FIGS. 1, 2 and 3.

FIG. 1 illustrates a rectangular package which comprises a backing 1 consisting of a paper label laminated with a polymeric film. The front part of the package consists of a vacuum formed polymeric film 2. These parts are bonded together to create a pocket 3 containing an item or items 4 that must be delivered sterile at operation.

Figure 1A:
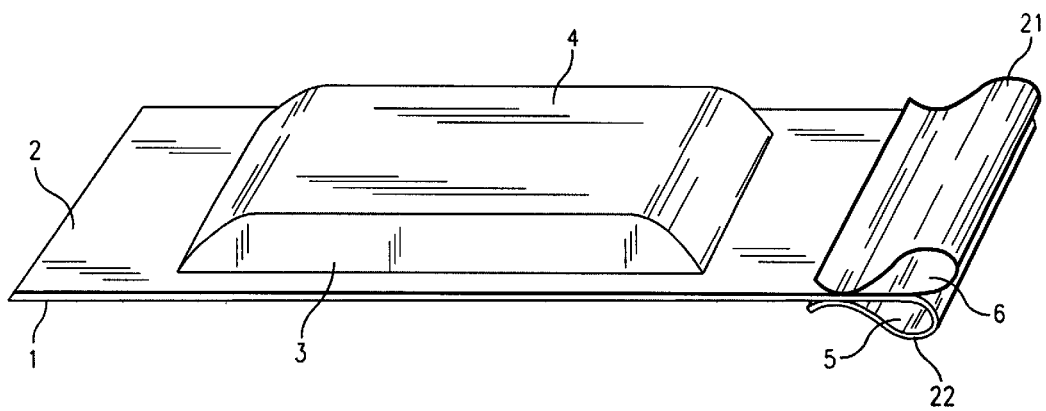
FIGS. 1A and 1B illustrate a preferred embodiment of a rectangular package formed of sterilized packaging material and containing a sterile item.
Figure 1B:
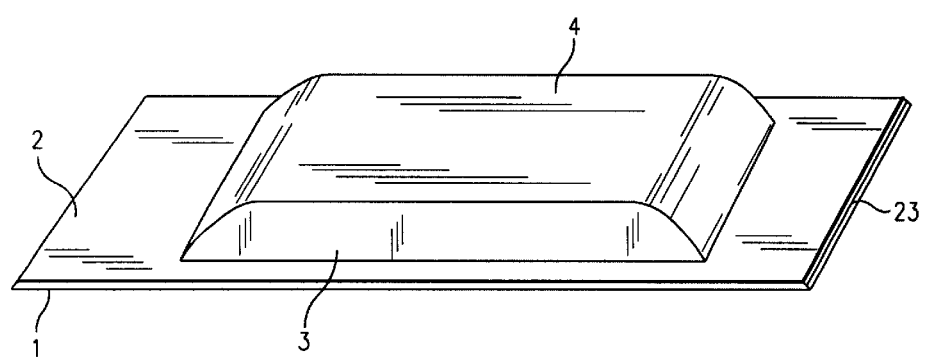

FIG. 1A illustrates another embodiment of the invention where tubular sections 21, 22 of paper, cardboard, metal or polymeric material may be fixed to the packaging 1, 2 so as to create openings 5, 6 which may be engaged by appropriate instrumentation which may be used to manipulate and open the packaging. In a further embodiment of the invention sections of paper, cardboard, metal or polymeric materials may be fixed to, or may protrude from the packaging 1, 2 to create tags 21, 22 which may be engaged by specifically designed or adapted instrumentation used to manipulate and open the packaging. The materials that form the packaging 1, 2 may be perforated to create openings 23 that may be engaged by appropriate instrumentation used to manipulate and open the packaging as shown in another embodiment of the invention in FIG. 1B.

At one end of the package, the backing 1 is folded onto itself to create a tubular opening 5 which runs along the length of the short side of the package. The front part of the package 2 is also folded onto itself to create a similar tubular opening 6.

FIG. 2 illustrates a dedicated instrument for manipulation and opening of the packet. The relatively heavy handle of the instrument 8 is provided with apertures for finger and thumb, resembling in this respect the handles of a pair of scissors. The arms of the instrument are hinged at a fulcrum point about one third of the way along the instrument by means of a rivet 9. A spring 10 holds the handles apart unless they are actually squeezed together.

At the functional end of the instrument the last section bends to form two extensions 12, running parallel to each other, and approximately perpendicular to the length of the instrument.

Each extension is shaped in cross section to fit into the openings of the "tubes" 5, 6 formed in the packaging material. The extensions are slightly longer than the tubes to permit the instrument to be fully inserted into the tubes. At the tip of each extension a small ledge 13 is created.

Approximately two thirds of the way along the instrument, and facing in the opposite directions to the extensions, there is positioned a protruding rest 14. When not in use the instrument balances upon this rest, and the relatively heavy handles 8.

Figure 3:
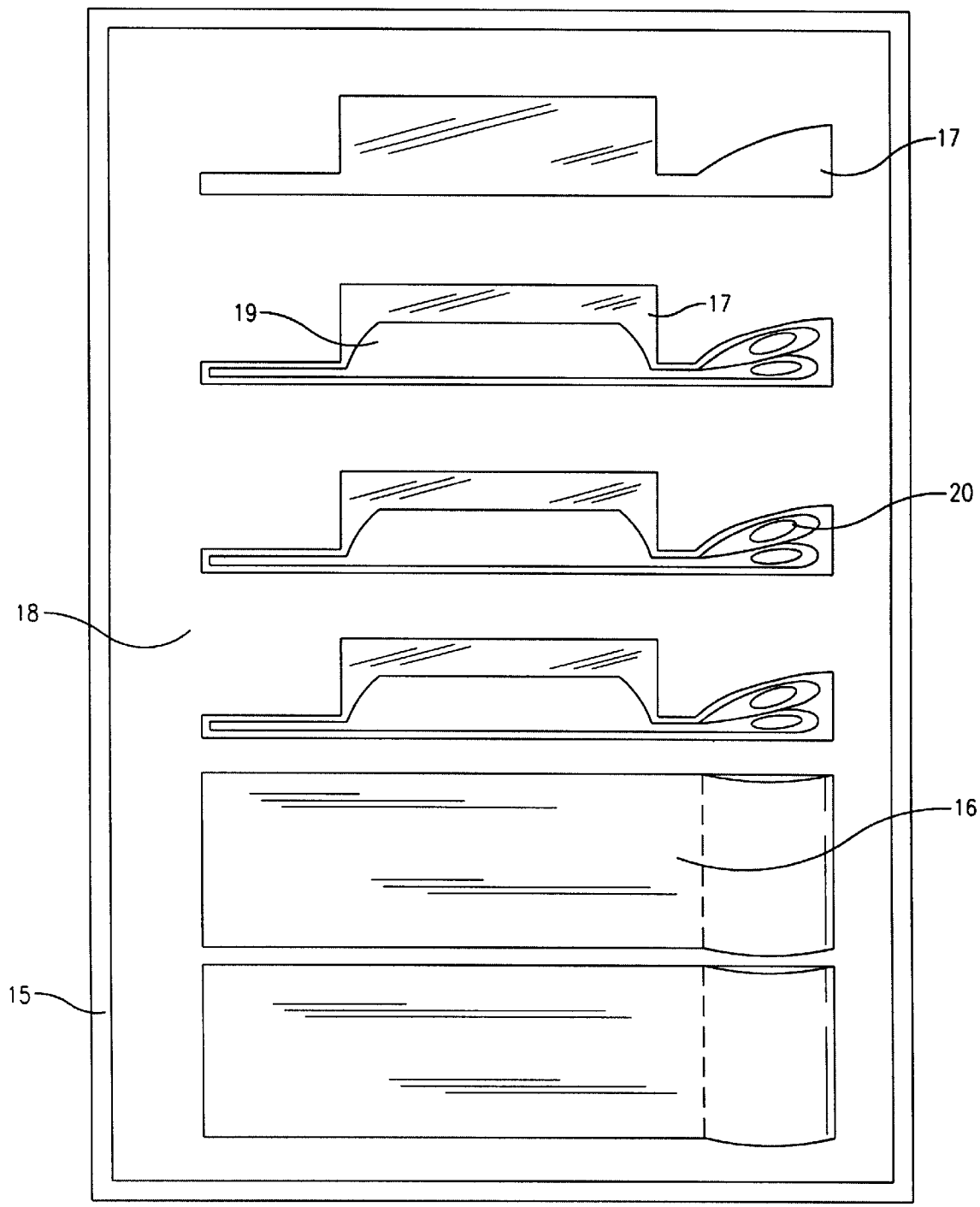
FIG. 3 illustrates a plan view of a preferred embodiment of the storage tray containing a number of packages.

FIG. 3 illustrates (plan view) a storage tray or organizer tray for packages of the type described in FIG. 1. The tray comprises a shallow cardboard box 15, having dimensions which will comfortably accommodate a row of several of the packages, which are stored and transported in a low profile, well protected position 16 in which the vacuum molded part of the package protrudes into the shallow box through a cut-out portion 17 of a cardboard support 18, which is recessed into the box.

The cut-out portion 17 in the cardboard support is also shaped to accommodate the package in an alternative orientation 19, in which the openings of the "tubes" 5, 6 formed in the parts of the packages may be easily accessed by the extensions of the instrument during a surgical procedure, thus effectively converting the storage tray into an organiser or rack.

The packages are raised off the base of the box by a small amount, and maintained in position by means of two slotted corrugated cardboard strips (not shown), which run between the cardboard support and the base of the box so that the ledges 13 at the tips of the instrument extensions 12 are able to pass beyond, and engage the packaging.

There is also provided a lid (not shown) that sits over the box and contents when the packages are in the "storage" position 16, so as to provide protection during transportation and storage.

In use, the surgeon carrying out the sterile procedure picks up the sterilised instrument in a gloved hand. Various packages containing a range of different items are prepositioned close by, or arranged in the appropriate storage rack, so that the openings of the tubes formed in the parts of the package may be easily accessed by the extension of the instrument.

The extensions of the instrument are inserted into the tubes formed in the parts of the package selected by the surgeon, so that the tips of the extensions protrude past the ends of the tubes. Gently squeezing the handles separates the extensions. The notched tips of the extensions then retain the package in place on the instrument.

The instrument is then held over a sterile surface; further pressure on the handles separates the front and back of the package along the relatively weakly bonded interface, and the contents of the package may then be emptied out.

After initial use the opened packaging is allowed to fall away from the instrument. The instrument is then replaced on the sterile surface, making sure that the extensions, which have now been in contact with the non-sterile exterior of the package do not contact other sterile items.

What is claimed is:

1. A packaging system, comprising:
   a number of packages, each package formed by sterilizable packaging material and enclosing a sterile item, the packaging material of each package having an opening formed thereon;
   a storage tray for containing the number of packages; and
   an instrument having functional extensions designed to engage, grasp, or mate with the opening formed on the packaging material,
   wherein an operator carrying out a surgical procedure, using a conventional aseptic surgical technique, uses the instrument to pick up, manipulate, and open the package to deliver the sterile item for use during the procedure.

2. The packaging system according to claim 1, wherein:
   the opening on the packaging material of each package is formed between a fold of the packaging material.

3. The packaging system according to claim 1, wherein:
   the opening on the packaging material of each package is formed by a perforation of the packaging material.

4. The packaging system according to claim 1, wherein:
   the opening on the packaging material of each package is formed by a tubular section of paper, cardboard, metal, or polymeric material fixed to the packaging material.

5. The packaging system according to claim 1, wherein:
   the instrument has a rest and a grip that together support the instrument when placed on a flat surface so that the functional extensions of the instrument will not contact the flat surface.

6. A packaging system, comprising:
   a number of packages, each package formed by sterilizable packaging material and enclosing a sterile item;
   a section of paper, cardboard, metal, or polymeric material fixed to the packaging material and forming a tag;
   a storage tray for containing the number of packages; and
   an instrument having functional extensions designed to engage, grasp, or mate with the tag,
   wherein an operator carrying out a surgical procedure, using a conventional aseptic surgical technique, uses the instrument to pick up, manipulate, and open the package to deliver the sterile item for use during the procedure.

* * * * *